United States Patent [19]

Jia et al.

[11] Patent Number: 5,684,103
[45] Date of Patent: Nov. 4, 1997

[54] COLOR STABLE DENTAL RESTORATIVE MATERIALS

[75] Inventors: Weitao Jia, Wallingford; Arun Prasad, Cheshire, both of Conn.

[73] Assignee: Jeneric/Pentron Incorporated, Wallingford, Conn.

[21] Appl. No.: 829,146

[22] Filed: Mar. 31, 1997

Related U.S. Application Data

[63] Continuation of Ser. No. 698,477, Aug. 15, 1996, abandoned, which is a continuation of Ser. No. 439,276, May 11, 1995, abandoned.

[51] Int. Cl.$^6$ .................................................. C08F 4/04
[52] U.S. Cl. ........................... 526/218.1; 526/219.2; 522/22
[58] Field of Search ..................... 526/218.1, 219.2; 522/28

[56] References Cited

U.S. PATENT DOCUMENTS

| | | |
|---|---|---|
| 3,488,846 | 1/1970 | Cornell . |
| 4,260,713 | 4/1981 | Tanaka et al. ............ 526/218.1 |
| 4,328,329 | 5/1982 | Novak ....................... 526/219.2 |
| 4,433,958 | 2/1984 | Fellman et al. . |
| 4,544,359 | 10/1985 | Waknine . |
| 4,547,531 | 10/1985 | Waknine . |
| 4,705,836 | 11/1987 | Ohtsuka et al. . |
| 4,937,175 | 6/1990 | White et al. ............ 526/218.1 |
| 5,276,068 | 1/1994 | Waknine . |
| 5,348,475 | 9/1994 | Waknine et al. . |

FOREIGN PATENT DOCUMENTS

| | | |
|---|---|---|
| 0 413 290 A2 | 2/1991 | European Pat. Off. . |
| 0103117 | 8/1981 | Japan ........................ 526/218.1 |
| 2 263 115 | 7/1993 | United Kingdom . |

OTHER PUBLICATIONS

Vazo® Polymerization Initiators Properties, Uses, Storage and Handling, DuPont, Jul., 1984.
Abstract, JP 62275103.
Textbook of Polymer Science by Fred. W. Billmeyer Jr. 1962 p. 264.
AN 1994: 86535 That Corresponds to JP05255030 by Yamamoto et al, 1993, Oct. 5 pp. 7 and 8.

*Primary Examiner*—Joseph L. Schofer
*Assistant Examiner*—N. Sarofim
*Attorney, Agent, or Firm*—Cummings & Lockwood

[57] ABSTRACT

In a polymerizable dental restorative resin composition useful as a dental composite resin and/or a denture/denture base material comprising at least one binder resin, a diluent monomer, at least one filler, optionally, a photopolymerization system comprising an initiator for initiating polymerization of the composite resin upon exposure to visible light and an accelerator, and an initiator for initiating polymerization of the composite resin upon application of heat, the improvement imparting shelf stability and substantially eliminating discoloration is provided comprising the initiator for initiating polymerization upon application of heat having the general formula:

$$R-N=N-R'$$

wherein R and R' can be the same or different, and are selected from the group consisting of oxygen-free aliphatic, cycloaliphatic, aromatic, and heterocyclic moieties.

16 Claims, No Drawings

COLOR STABLE DENTAL RESTORATIVE MATERIALS

This application is a continuation of application Ser. No. 08/698,477, filed Aug. 15, 1996, which is a continuation of application Ser. No. 08/439,276, filed May 11, 1995.

This invention relates to improved polymeric products which have been found useful as dental restorative materials, e.g., dental composite resins and denture base materials. More specifically, the improved polymeric products are filled resin compositions which, depending upon filler content, are useful as crown and bridge materials, either with an alloy substrate or without a substrate, or as reconstruction materials, bioprostheses, filling materials, inlays, onlays, laminate veneers, dentures, and denture base materials.

BACKGROUND OF THE INVENTION

The practice of dentistry includes the preparation and application in the oral environment of artificial dentures and restorations of tooth structure for example, veneers, inlays, onlays, crowns, and bridges. Historically, the dental profession has used several different types of materials for aesthetic restorative purposes. Dental composite materials, which are particularly preferred for the purpose of aesthetic restorations, and dentures and denture base materials, include an organic or inorganic filler component and an organic matrix component such as a polymerizable monomer. Such composites typically comprise, for example, an acrylic or methacrylic based system in which a silica or silicate glass is bonded to the resin matrix or to a coupling agent which is bonded to both.

Dental restorations are typically prepared from dental restorative materials comprising an appropriate filled resin by forming the restoration on a laboratory working model die made from an intraoral impression replica or alloy substrate and curing the restorative material. Dentures and/or denture base materials are formed by compression or injection molding techniques and curing the material in the mold by heating at about 80° C., typically, with or without water, pressure, vacuum, or a combination thereof for less than about 15 minutes. The dental restorative materials currently in use are formed into useful end products by the conversion of monomers and/or oligomers into a polymerization matrix by heat, chemical, or photochemical initiation to form free radicals and thereby effect polymerization.

It is an object of the present invention to provide improved dental restorative materials especially useful as dental composite resins and/or dentures or denture base materials which are storage-stable and not prone to discoloration and which can be polymerized by heat in combination with or without water, pressure and/or vacuum. In addition, the improved dental restorative materials of the present invention can be cured by such trimodal curing methods employing visible light cure, heat, and vacuum as described in U.S. Pat. No. 5,348,475.

It is another object of the present invention to provide storage-stable dental restorative materials which are not prone to discoloration upon aging by eliminating the use of the peroxide initiators typically employed as thermal initiators and substituting in lieu thereof bisazo initiators having the general formula:

wherein R and R' can be the same or different and are selected from the group consisting of oxygen-free aliphatic, cycloaliphatic, aromatic, and heterocyclic moieties.

SUMMARY OF THE INVENTION

These as well as other objects are accomplished by the present invention, which provides an improved polymerizable dental restorative resin composition comprising at least one binder resin, a diluent monomer, optionally a photopolymerization system comprising an initiator for initiating polymerization of the restorative resin upon exposure to visible light and an accelerator, at least one filler, and an initiator for initiating polymerization of the resin upon application of heat, wherein the improvement resides in the use of a bisazo initiator, said bisazo initiator having the general formula:

wherein R and R' can be the same or different and are selected from the group consisting of oxygen-free aliphatic, cycloaliphatic, aromatic and heterocyclic moieties.

DETAILED DESCRIPTION OF THE INVENTION

The polymerizable dental restorative resin compositions useful in the present invention are not particularly limited and comprise broad spectrum polymer blends comprising binder resins, diluent monomers, fillers, and a heat cure system. The blends can also optionally include antioxidants, shelf life stabilizers, a photosensitizing system, pigments, opacifiers, handling agents and other modifiers as will be readily appreciated by those of skill in the art.

The polymerizable dental restorative resin compositions of the present invention comprise at least one polymerizable binder resin. The polymerized resin preferably has sufficient strength and hydrolytic stability to make it suitable for use in the mouth. Acceptable functional resins will be familiar to those skilled in the art, and include acrylate, methacrylate, urethane acrylate, bisphenol A diglycidylmethacrylate and the like, such as those disclosed in U.S. Pat. No. 5,276,068, the pertinent portions of which are incorporated herein by reference. A preferred polymerizable resin for use in the present invention is a mixture of urethane dimethacrylate (frequently referred to as "UDMA"), polycarbonate dimethacrylate (frequently referred to as "PCDMA") and triethyleneglycol dimethacrylate (frequently referred to as "TEGDMA").

Other suitable binder resins include a wide variety of ethylenically unsaturated polymerizable compositions, including the bis-glycidyl-methacrylate adduct of bisphenol A (Bis-GMA) and its acrylic counterparts. Alternatively, the adducts of 2,2,3-trimethylhexane diisocyanate with hydroxyethyl methacrylate, hydroxypropyl methacrylate and other hydroxyalkyl acrylic species are also preferred. Those skilled in the art will appreciate that other acrylated polyesters can also be suitable. Such acrylated polyesters can also be reacted with isocyanates to form urethanes useful as binder resins. Thus, Bis-GMA can be reacted with a diisocyanate (or other isocyanate) such as hexamethylene diisocyanate, phenylene diisocyanate or a wide variety of other aliphatic and aromatic diisocyanates to provide useful binder resins.

A particularly preferred binder resin comprises an admixture of a polycarbonate dimethacrylate and a second resin, such as Bis-GMA and/or urethane dimethacrylate, or oligomers thereof, wherein, for example, the polycarbonate dimethacrylate comprises the condensation product of triethylene glycol bis(chloroformate) and 2-hydroxyethyl methacrylate.

The dental restorative composition will also typically include a diluent monomer to increase the surface wettability of the composition by decreasing the viscosity of the polymerization medium and increasing the contact angle of the droplet in order to attain a more manageable working viscosity. Further, such diluents can be used as crosslinking agents.

Viscosity control which is well within the skill of the art will be understood to result in moldable, workable materials suitable for a wide range of dental restorative uses. Diluent monomers can be any of a wide range of polymerizable monomers capable of sustaining photochemically and heat initiated polymerization. Preferably, the diluents will be the hydroxyalkyl methacrylates such as 2-hydroxyethylmethacrylate and 2-hydroxypropylmethacrylate; ethyleneglycolmethacrylates, including ethyleneglycolmethacrylate, diethyleneglycolmethacrylate, triethyleneglycolmethacrylate and tetraethyleneglycolmethacrylate; diisocyanates, hexamethylene diisocyanate and ethoxylated monomers such as 1,6-hexanedioldimethacrylate. 2-hydroxyethylmethacrylate (2-HEMA) and/or triethyleneglycolmethacrylate (TEGDMA) are particularly preferred.

The fillers utilized in the dental restorative compositions of the present invention can be selected from any of the fillers conventionally used in the dental industry capable of being covalently bonded to the resin matrix itself or to a coupling agent which is covalently bonded to both. Among those fillers which are especially suited in the practice of this invention are the alkali metal or alkaline earth metal silicates, such as lithium silicate, barium silicate, and the like. Other examples of suitable filler materials include, but are not limited to, silica, silicate glass, quartz, strontium silicate, borosilicate, amorphous silica, alumina, zirconia, and tin oxide. Particularly suitable fillers for dental restorative materials prepared in accordance with the present invention are those having a particle size ranging from about 0.01 to about 10.0 μm with a silicate colloid of 0.001 to about 0.07 μm and prepared by a series of milling steps comprising wet milling in an aqueous medium, surface etch milling, and silanizing milling in a silane solution. Some of the aforementioned inorganic fillers are described in U.S. Pat. Nos. 4,544,359 and 4,547,531, the pertinent portions of which are hereby incorporated by reference. Organic fillers such as polymethylmethacrylate, methyl methacrylate copolymer, polyethylmethacrylate, ethyl methacrylate copolymer, and the like can be similarly employed.

Those skilled in the art will appreciate that the amount of filler loading which can be accomplished with a given resin system will vary depending upon several factors, including the identity of the resins and fillers and the particle sizes of the filler. It should be appreciated that, for a given resin system, an appropriate filler must be chosen. For example, the filler selected must be such that the transmission of visible or ultraviolet light by the restorative composition must be sufficient for polymerization to take place. Persons skilled in the art will be able to select fillers and determine filler particle sizes based upon this requirement.

The dental restorative compositions of the present invention can optionally include a photosensitizing system for inducing polymerization of the resin monomers and/or oligomers by the action of visible light. The polymerization initiators usable in the dental restorative compositions are conventional visible light cure initiators well known in the art. Light sensitive compounds such as benzyl, diketones and d,l-camphoroquinone are preferred, with camphoroquinone being particularly preferred.

The dental restorative composition can also optionally include an organic tertiary amine reducing agent as a visible light polymerization accelerator. Numerous tertiary amines are useful as reducing agents for inclusion in the present invention; however, the tertiary amines are generally acrylate derivatives such as dimethylaminoethylmethacrylate and diethylaminoethylmethacrylate.

The improvements in storage stability and the substantial elimination of discoloration in the composite resins of the present invention are attributable to the bisazo initiators used in lieu of the conventional peroxide initiators. The bisazo initiators of the present invention have the following general formula:

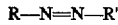

R—N=N—R' wherein R and R' can be the same or different and are selected from the group consisting of oxygen-free aliphatic, cycloaliphatic, aromatic, and heterocyclic moieties. Illustrative of such suitable bisazo initiators are 2,2'azobis (2,4-dimethylpentanenitrile), 2,2'azobis (2-methyl propane nitrile), 2,2'-azobis (2-methylbutanenitrile), 1,1'-bisazo (cyanocyclohexane), azobisisobutyronitrile, azobenzene, 1,1'(azodimethylene) dipiperidine, and the like.

Of the foregoing azobis initiators, the azobisnitriles are preferred. The azobis aliphatic nitriles are most preferred, especially the VAZO® polymerization initiators available from E.I. du Pont de Nemours, Wilmington, Del. For example, VAZO 52-2,2'-azobis(1,4-dimethylpentanenitrile); VAZO 64-2,2'-azobis (2-methylpropanenitrile); VAZO 67-2, 2'azobis (2-methybutanenitrile), VAZO 88-1,1'-azobis (cyanocyclohexane), and the like have been found useful.

The incorporation of the thermal initiators of the present invention into the polymerizable dental restorative materials enhances the shelf life and color stability thereof. The amount of polymerization initiator employed is sufficient to permit rapid polymerization upon exposure to temperatures ranging from about 45° to about 120° C. (for example, in boiling water) in less than about 15 minutes. Preferably, the amount of polymerization initiator ranges from about 0.01 to 5 weight percent of the restorative resin composition and most preferably ranges from about 0.01 to 2 weight percent of the restorative resin composition.

Pigments, ultraviolet light absorbers, opacifiers, brightening agents and antioxidants/shelf life stabilizers, i.e., BHT, and other additives can be included in the restorative compositions of the invention without departing from its spirit.

The methods of preparing dental restorations and/or dentures or denture base materials in accordance with the present invention involve the preparation thereof from the filled polymerizable restorative resin compositions in accordance with known techniques. Cure can be effected by heat with or without water, pressure, and/or vacuum. If desired, cure can be effected at least partially with visible light, and then the cure can be completed in a heat/vacuum cure step as described in U.S. Pat. No. 5,348,475, the pertinent portions of which are incorporated herein by reference.

The preparation of a restoration can be done intraorally by the dentist, for example, for simple veneers, inlays, and onlays, or extraorally by a dental laboratory, on a stone model or rigid polyvinylsiloxane made from an intraoral impression replica or onto an alloy substrate (foil or cast).

In one embodiment, when building a restoration intraorally or on a working model, a releasing agent is applied onto the tooth structure or model, respectively, overlapping the cavosurface margin. As an optional technique, the restoration should be removed from the model after each layer is built up and cured, and the releasing agent reapplied before the addition of the next layer, being careful not to entrap release agent between composite layers. Suitable releasing agents include a combination of mineral oil and methanol, hydrophilic silicon-type surfactants, or various hydrophilic oil lubricants.

Upon completion of the restoration, the restoration can be trimmed and polished in accordance with well established techniques, after which the restoration is subjected to a further curing step. This curing step involves subjecting the restoration to dry heat under vacuum (or an oxygen inhibited environment) for a sufficient amount of time to effect complete curing of the composite resin. More specifically, the restoration is placed into a heat/vacuum chamber, either with or without the die, which has been preheated to the appropriate temperature, and the chamber is evacuated for a period of time ranging from about 10 to about 30 minutes, preferably from about 10–20 minutes. The curing is effected at a temperature which is at or near the glass transition temperature of the dental restorative material. A temperature of about 225° F. (107° C.) is preferred, but is not limiting. The pressure within the vacuum chamber should be from about 27 to about 29.5 in. Hg, and preferably is maintained at about 28.5–29.5 in. Hg during the curing process. This anaerobic environmental chamber near Tg attains a greater Dp, and polymer chain orientation leads to further semicrystallinity attaining greater toughness and elimination of residual surface monomeric layers.

The CONQUEST curing oven, available from Jeneric/Pentron, Inc. of Wallingford, Conn., is particularly well suited for the heat/vacuum curing, although other suitable heat/vacuum chambers can also be employed.

Upon removal from the heat/vacuum oven, the restoration should be bench hardened for at least several minutes prior to further handling. Preparation of the restoration for placement in the oral environment is in accordance with conventional techniques, for example, by sandblasting the interior surface of the restoration with aluminum oxide, using wax or a rubber-sep type product to protect the glaze finish. The thus-prepared restorations can be bonded intraorally using any of the commercially available bonding agents, luting cement systems, and the like, the selection of which is well within the skill of the art.

Denture base material and dentures can be fabricated from the dental restorative materials of the present invention by incorporation of suitable pigments therein to simulate natural gum tissue color. The restorative materials can be compression molded or injection molded into conventional working molds employing such techniques as described in *Skinner's Science of Dental Materials*, 9th Edition. Thereafter, cure can be effected in the mold by heating, for example, at 80° C. with or without water, pressure, and/or vacuum for less than about 15 minutes.

The present invention will be more clearly understood from the following specific examples.

In the following examples, the color of a material is determined by a colorimeter which detects color parameters or coordinates L, a and b as specified by DIElab (CIE, 1978). There are five most common and recognized indices which can be computed from the L, a and b. Among them, the Total Color Difference is the magnitude of the resultant vector of three component differences: L(+ΔL=Lighter), a(+Δa=Redder) and b(+Δb=Yellower). The total magnitude of color difference E between two colors can be computed from the equation:

$$E = \sqrt{(\Delta L)^2 + (\Delta a)^2 + (\Delta b)^2}$$

The Yellowness Index, YI, is intended primarily for determining the degree of yellowness for certain nearly colorless transparent plastics, nearly white translucent, or opaque plastics. It is determined in accordance with ASTM method D1925 as follows:

$$YI = \frac{71.53a + 178.82b}{L}$$

Using the color indices calculated from the color coordinates L, a and b, the color change of the material can be determined.

EXAMPLE 1

100 grams of a monomeric matrix composition was prepared by admixing the following:

40 grams triethyleneglycoldimethacrylate 35 grams urethane dimethacrylate 25 grams polycarbonate dimethacrylate [the polycondensation reaction product of 2-hydroxyethyl methacrylate and triethyleneglycol bis (chloroformate)].

2.0 grams VAZO 88-1,1'-azobis (cyanocyclohexane) available from E.I. Du Pont de Nemours, Wilmington, Del.

0.75 grams UV-5411 [2-(2-hydroxy-5-tert.-octylphenyl] benzotriazole available from American Cyanamid Co., Stamford, Conn.

0.05 grams benzoylhydroxytoluidine (BHT).

0.01 grams 2,2'-(2,5thiophenediyl)bis(5-tert.-butylbenzoxazole).

Filler Material Preparation:

A bariumborosilicate glass flit (SP1650) was processed and treated as described in U.S. Pat. No. 5,276,068. The resulting filler exhibited an average particle size of 0.6 micron and a silane content of about 6.5%.

A filled composite material of the present invention especially suitable for fabrication of denture base material, denture teeth and inlay/onlays, veneers, and other dental appliances in a dental laboratory was prepared by admixing 25% by weight of the foregoing monomeric matrix composition with 70% by weight of the inorganic filler as prepared above and 5% by weight of colloidal fumed silica having an average particle size of about 0.04 micron. The resulting composite was a homogeneous paste comprising the monomeric composition as the matrix with the inorganic filler and the fumed silica uniformly dispersed therein.

The resulting material was then subjected to aging in a 37° C. convection oven for 2 weeks and 1 month. A small portion of the material was also put into a Cure-Lite light curing unit (Jeneric/Pentron, Inc., Wallingford, Conn.) for 1 minute light exposure. At each test stage, the material was observed visually and then made into 1 mm thick and 20 mm in diameter disc samples and cured with heat only in a Conquest C&B Curing Unit (Jeneric/Pentron, Inc.) for 15 minutes. Then, the color coordinates L, a and b of the samples were determined by a Colorgard 05 colorimeter (Pacific Scientific Co., Calif.).

As a comparison, two identical materials as above were prepared except the VAZO 88 initiator was replaced by (1) 1.0 gram benzoyl peroxide, and (2) 2.0 grams benzoyl peroxide. The control materials were also subject to test in the same manner as for the present invention.

Set out below in Table 1 are the test results.

TABLE 1

| Test Condition | Type of Heat Cured Initiator in Material | | |
| --- | --- | --- | --- |
| | 2.0 VAZO 88 | 1.0 BPO | 2.0 BPO |
| Intensive Light Exposure Test Material at Fresh Stage | No Effect on Material All Show No Color Change Visually same at Starting Point) | Material Thickened | Partially Hardened (Color is the |
| YI after Cure | 45.6 | 48.9 | 49.8 |
| 2 wks at 37° C. Color Change | No | Yes | Yes |
| YI after Cure | 45.6 | 54.5 | 64.5 |
| 4 wks at 37° C. Color Change | No | Yes | Yes |
| YI after Cure | 45.8 | 57.7 | 71.7 |

The above data show that with the aging process, materials containing benzoyl peroxide exhibit unstable characteristics, which are reflected by color change and Yellowness Index increase. Upon intensive light exposure for one minute, the material containing BPO also shows signs of polymerization. On the other hand, the material with VAZO 88 heat activated free radical initiator exhibited no noticeable change in color demonstrating its stability.

EXAMPLE 2

Employing the trimodal curing method of U.S. Pat. No. 5,348,475, a cured single paste dental restorative composition was prepared as described in Example 1, except 0.1 grams d,l-camphoroquinone and 0.2 grams diethylamino ethylmethacrylate (DEAEMA) were additionally admixed into the resin matrix composition.

The trimodal curing technique involves the use of visible light illumination for the initial curing of the composite resin and a combination of dry heat and vacuum for the complete cure of the composite restorative material.

The resulting composite material was then subjected to aging at 37° C. for 2 weeks. At the fresh and aged stages, the material was made into 1 mm thick and 20 mm in diameter discs with visible light cure first and then processed in a Conquest Heat/Vacuum Unit for 15 minutes. A computerized colorimeter Colorgard 05 System was utilized to observe the samples and the color coordinates L, a and b were determined.

As a comparison, two additional compositions were prepared in the same way as the present invention except (1) the VAZO 88 initiator was substituted by BPO, and (2) the composition was prepared without any heat initiator. The formulated materials were then subjected to the same aging treatment as above.

Set out below in Table 2 are the testing results of Total Color Difference E, which is present between the fresh and the aged materials, and the Yellowness Index (YI).

TABLE 2

| Material | Color | Type of Heat Initiator in the Composite | | |
| --- | --- | --- | --- | --- |
| Status | Parameter | 2.0 VAZO 88 | 2.0 BPO | 0 Heat Initiator |
| Not Aged Composite (VLC/HV) | L | 16.88 | 16.95 | 16.97 |
| | a | −12.10 | −12.16 | −12.71 |
| | b | 8.95 | 10.04 | 9.35 |
| | YI = | 43.5 | 54.6 | 45.1 |
| 2 Weeks | L | 17.01 | 17.30 | 17.00 |
| Aged Composite (VLC/HV) | a | −11.96 | −13.11 | −12.66 |
| | b | 8.91 | 11.92 | 9.25 |
| | YI = | 43.4 | 69.0 | 46.0 |
| | E = | 0.20 | 2.16 | 0.12 |

The above data illustrate that the presence of the heat initiator VAZO 88 in the composite imparts similar color stability to the composition without any heat initiator. On the other hand, the composition containing conventional heat initiator BPO showed severe discoloration. [Generally, when the color difference E between two colors is less than one (1), more than 50% of observers will judge those two colors as matching.] The dramatic increase in YI of the composition containing BPO upon aging also indicates the color unstable nature of the benzoyl peroxide.

EXAMPLES 3–5

Example 2 is repeated except that the VAZO 88 heat initiator is replaced by VAZO 52 (Example 3), VAZO 64 (Example 4), and VAZO 67 (Example 5). In each instance, the resulting dental restorative materials are compared to identical compositions containing benzoyl peroxide as the initiator and a composition containing no heat initiator. In each instance, results substantially similar to those reported in Example 2 are obtained.

EXAMPLE 6

A heat curable single paste denture base material is prepared in the same manner as described in Example 1, except 0.024 gm. Red #40 and 0.008 gm. Red #5595 pigments are added to simulate natural gum tissue color. The resulting denture base material is compression molded in a dental base working mold, and cure is effected in the mold at 80° C. for about 15 minutes and compared to identical compositions containing BPO as the initiator. In each case, results substantially similar to those reported in Example 1 are obtained.

Although the present invention has been described using illustrative examples, it should be understood that the invention is not limited to the specific exemplary embodiments shown herein. Various modifications and alterations of this invention will be apparent to those skilled in the art without departing from the scope and spirit of this invention.

What is claimed is:

1. A polymerizable dental restorative resin composition comprising at least one binder resin, a diluent monomer, at least one filler, optionally a visible light photopolymerization initiator and an accelerator for initiating polymerization of the composite resin upon exposure to visible light, and an initiator for initiating polymerization of the composite resin upon application of heat, wherein the initiator for initiating polymerization upon application of heat consists of 1,1'-bisazo (cyanocyclohexane).

2. A polymerizable dental restorative resin composition as defined in claim 1 wherein the binder resin comprises a polycarbonate dimethacrylate condensation product obtained by the condensation reaction of an hydroxyalkyl methacrylate and a bis (chloroformate).

3. A polymerizable dental restorative resin composition as defined in claim 2 wherein the binder resin additionally comprises bisglycidyl methacrylate.

4. A polymerizable dental restorative resin composition as defined in claim 2 wherein the binder resin additionally comprises a urethane dimethacrylate.

5. A polymerizable dental restorative resin composition as defined in claim 3 wherein the binder resin additionally comprises a urethane dimethacrylate.

6. A polymerizable dental restorative resin composition as defined in claim 1 wherein the diluent monomer is 1-hydroxyethylmethacrylate.

7. A polymerizable dental restorative resin composition as defined in claim 4 wherein the diluent monomer is triethyleneglycoldimethacrylate.

8. A polymerizable dental restorative resin composition as defined in claim 1 wherein the filler has an average particle size ranging from about 0.01 to 10.0 µm.

9. A polymerizable dental restorative resin composition as defined in claim 1 wherein the filler is an inorganic filler.

10. A polymerizable dental restorative resin composition as defined in claim 1 wherein the filler is an organic filler.

11. A polymerizable dental restorative resin composition composition as defined in claim 1 wherein the initiator for initiating polymerization upon application of heat is present in an amount sufficient to permit polymerization upon exposure to temperatures ranging from about 45° to about 120° C. in less than about 15 minutes.

12. A polymerizable dental restorative resin composition as defined in claim 11 wherein the initiator is present in an amount ranging from about 0.01 to 5 weight percent based on the weight of the resin composition.

13. A polymerizable dental restorative resin composition composition as defined in claim 12 wherein the initiator is present in an amount ranging from about 0.01 to 2 weight percent based on the weight of the resin composition.

14. A dental composite resin composition comprising the polymerizable dental restorative resin composition as defined in claim 1.

15. A denture base composition comprising the polymerizable dental restorative resin composition as defined in claim 1.

16. A denture composition comprising the polymerizable dental restorative resin composition as defined in claim 1.

* * * * *